United States Patent
Koptis et al.

(10) Patent No.: US 8,591,130 B2
(45) Date of Patent: Nov. 26, 2013

(54) LEAK RESISTANT APPLICATOR POD AND METHOD

(76) Inventors: Kurt Koptis, Auburn, CA (US); Bruce Bodlak, Folsom, CA (US)

( * ) Notice: Subject to any disclaimer, the term of this patent is extended or adjusted under 35 U.S.C. 154(b) by 365 days.

(21) Appl. No.: 12/988,610

(22) PCT Filed: Apr. 22, 2009

(86) PCT No.: PCT/US2009/041324
§ 371 (c)(1),
(2), (4) Date: Oct. 19, 2010

(87) PCT Pub. No.: WO2009/132052
PCT Pub. Date: Oct. 29, 2009

(65) Prior Publication Data
US 2011/0033221 A1    Feb. 10, 2011

Related U.S. Application Data

(60) Provisional application No. 61/125,136, filed on Apr. 22, 2008.

(51) Int. Cl.
*B43K 5/14* (2006.01)

(52) U.S. Cl.
USPC ............................... 401/133; 401/132; 604/3

(58) Field of Classification Search
USPC ............. 401/132–135, 196; 604/3, 306, 310; 206/209, 210, 361; 222/153.02–153.07
See application file for complete search history.

(56) References Cited

U.S. PATENT DOCUMENTS

| | | | |
|---|---|---|---|
| 3,369,267 A * | 2/1968 | Friedland et al. | 15/104.94 |
| 3,386,793 A * | 6/1968 | Stanton | 401/132 |
| 3,429,429 A | 2/1969 | Poitras | |
| 3,431,919 A * | 3/1969 | Van Der Bosch | 132/317 |
| 3,647,305 A | 3/1972 | Baker et al. | |
| 3,981,304 A * | 9/1976 | Szpur | 604/3 |
| 3,998,559 A * | 12/1976 | Hoyt | 401/132 |
| 4,140,409 A * | 2/1979 | DeVries | 401/132 |
| 4,360,020 A * | 11/1982 | Hitchcock et al. | 604/289 |
| 4,430,013 A | 2/1984 | Kaufman | |
| 4,629,080 A | 12/1986 | Carveth | |
| 4,648,506 A | 3/1987 | Campbell | |
| 4,696,393 A | 9/1987 | Laipply | |
| 4,740,194 A * | 4/1988 | Barabino et al. | 604/3 |
| 4,805,767 A | 2/1989 | Newman | |
| 4,812,067 A * | 3/1989 | Brown et al. | 401/132 |
| 4,896,768 A | 1/1990 | Anderson | |

(Continued)

FOREIGN PATENT DOCUMENTS

WO    WO2004101423    11/2004

*Primary Examiner* — David Walczak
*Assistant Examiner* — Jennifer C Chiang
(74) *Attorney, Agent, or Firm* — David M. Lang; Law Offices of David M. Lang (57) ABSTRACT

An applicator apparatus having a sealed container pod which may be opened through an actuating tab. In certain embodiments the terminal end of the open package covered by an applicator surface that may be adherently affixed to the container pod. In certain embodiments, actuating tab passes through a void defined by a suitably shaped applicator surface. Certain embodiments describe a rupturable seal permitting mixing of contents within the container pod before distribution to applicator surface. A method for applying material to a desired surface, and method of applying a therapeutic substance to a desired tissue is disclosed.

3 Claims, 5 Drawing Sheets

(56) References Cited

U.S. PATENT DOCUMENTS

| | | | |
|---|---|---|---|
| 4,917,676 A * | 4/1990 | Heiber et al. ............... 424/449 |
| 4,921,137 A | 5/1990 | Heijenga |
| 5,287,961 A | 2/1994 | Herran |
| 5,320,217 A * | 6/1994 | Lenarz ........................ 206/209 |
| D351,338 S | 10/1994 | Koptis |
| D363,377 S | 10/1995 | Koptis |
| 5,487,932 A | 1/1996 | Dunshee |
| 5,558,874 A * | 9/1996 | Haber et al. ............... 424/402 |
| 5,577,851 A | 11/1996 | Koptis |
| D386,854 S | 11/1997 | Koptis |
| D387,563 S | 12/1997 | Koptis |
| D398,235 S | 9/1998 | Koptis |
| 6,007,264 A * | 12/1999 | Koptis ......................... 401/132 |
| 6,508,604 B1 * | 1/2003 | Bechmann et al. .......... 401/132 |
| 6,726,386 B1 | 4/2004 | Gruenbacher et al. |
| 6,789,971 B2 * | 9/2004 | Tsaur ........................ 401/133 |
| 6,805,263 B2 * | 10/2004 | Garcia et al. ............... 222/145.1 |
| 6,846,297 B2 * | 1/2005 | Lin ........................... 604/1 |
| 6,902,335 B2 * | 6/2005 | Bergey et al. ............... 401/132 |
| 7,059,542 B2 * | 6/2006 | Garcia et al. ............... 239/327 |
| 7,179,007 B2 | 2/2007 | Wong et al. |
| 7,325,703 B2 * | 2/2008 | Gherdan et al. ............. 222/94 |
| 7,458,741 B2 | 12/2008 | Detwiler et al. |
| 7,506,762 B2 * | 3/2009 | Nelson et al. ............. 206/484.1 |
| 7,523,821 B2 * | 4/2009 | Assie et al. ................. 206/204 |
| 7,552,823 B2 * | 6/2009 | Schuehrer ................... 206/484 |
| 7,963,712 B2 * | 6/2011 | Sogaro ....................... 401/133 |
| 8,113,730 B2 * | 2/2012 | Maloney et al. ............. 401/133 |
| 8,262,305 B2 * | 9/2012 | Lam et al. .................. 401/133 |
| 2003/0094466 A1 * | 5/2003 | Duquet et al. ............... 222/212 |
| 2005/0047845 A1 * | 3/2005 | White et al. ................ 401/132 |
| 2005/0207821 A1 | 9/2005 | Bergey et al. |
| 2006/0067783 A1 * | 3/2006 | Tsaur ........................ 401/132 |
| 2006/0247568 A1 * | 11/2006 | Stenton ...................... 604/3 |
| 2006/0283727 A1 | 12/2006 | Nelson et al. |
| 2007/0048062 A1 | 3/2007 | Berger Sharp et al. |
| 2007/0048063 A1 * | 3/2007 | Bauer et al. ................ 401/7 |
| 2007/0068845 A1 | 3/2007 | Schuehrer |
| 2007/0189835 A1 * | 8/2007 | Klocke et al. ............... 401/133 |
| 2009/0123217 A1 * | 5/2009 | Ross ......................... 401/134 |

\* cited by examiner

LEAK RESISTANT APPLICATOR POD AND METHOD

CROSS-REFERENCE TO RELATED APPLICATIONS

This application claims the benefit under 35 U.S.C. §119(e), to U.S. Provisional Application 61/125,136 filed Apr. 22, 2008, entitled "EASY OPEN APPLICATOR POD" and PCT/US09/41324 filed on Apr. 22, 2009, which is incorporated by reference in its entirety and made part of this specification.

FIELD OF THE INVENTION

The present invention relates to applicators generally, and more specifically to apparatus and methods directed toward storage of and application of a substance which may be distributed onto a surface of interest.

BACKGROUND

The prior art includes packaging materials permitting a substance to be contained within and distributed onto a surface of interest. For example U.S. Pat. No. 6,007,264 to Koptis discloses, in part, a container with a pair of built-in, outwardly pivotable flaps which form a package applicator that may be unsealed through squeezing the container or pulling the flaps apart, or by tearing, unblocking, or unfolding the flaps. U.S. Pat. No. 6,726,386 to Gruenbacher et al. discloses, in part, an applicator for distributing a substance onto a target surface wherein the product has a reservoir that releases product via application of pressure to the reservoir.

Prior art solutions have the favorable characteristics of permitting easy transportation and application of a relatively small amount of product when and where opportune. Some aspects of prior art solutions, however, are particularly vulnerable to inadvertent product release and leakage where a compressible force increases the intracompartmental pressure sufficient to overcome such threshold needed to trigger product release. Inadvertent product leakage not only results in wasted material but may soil the interior or a purse or handbag or other environment where the container was located, as well as potentially damaging or destroying any items contained therein. This is particularly true where the product itself may cause staining, is caustic, or is highly reactive in nature. What is therefore needed is a product packaging that is more stable when subjected to inadvertent compressible forces and will more reliably dispense and apply product when and where the user selects.

SUMMARY

One aspect of certain embodiments of the present invention provides for a container pod which is capable of holding material and releasing it when a user actuates a tear tab to open the package and dispense the material onto an applicator surface such as a sponge. Another aspect of certain embodiments of the present invention facilitates multidirectional application of material to a surface of interest. Other embodiments disclose applicator packaging allowing different materials to be packaged together, mixed just prior to use, and applied to a surface of interest. Other embodiments disclose reinforcing and stabilizing mechanisms resulting in a more firm applicator that is less subject to container collapse and obstruction of product flow. Further, the inventive applicator having a thin, slender profile and being less vulnerable to rupture, provides an efficient way to package numerous units of product and offers ideal way to provide a usable volume of sample in locations where compression is likely, such as a magazine or periodical.

DETAILED DESCRIPTION

Figure 1:
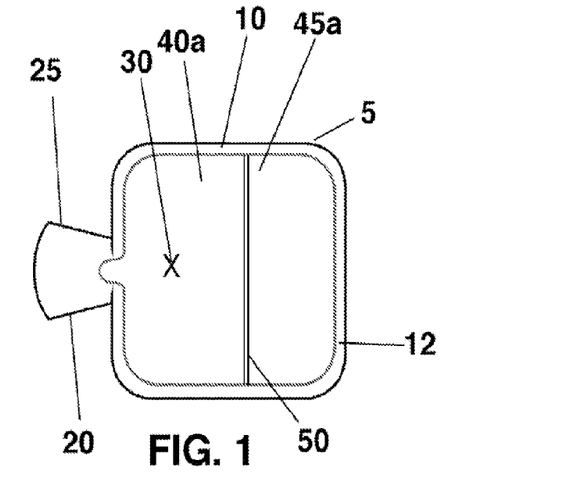
FIG. 1 is a top view of one dual absorptive surface embodiment of the present invention, and optional embodiment dividing seam.

Turning now to the illustrations, FIG. 1 depicts an embodiment containing and dispensing applicator apparatus 5 generally. Container pod 10 has a top surface, bottom surface, front surface, and end surface, and may be comprised of two substantially identical opposing perimetrically sealed layers 12. At least a portion of said container includes an openable seal 15 which is operatively coupled to and actuated by actuating tab 20. When tab 20 is pulled with sufficient force, openable seal 15 is ruptured and container pod 10 opens. Flowable contents contained within pod 10 may naturally flow or may be expressed or extruded from within said container 10 onto applicator surface 30, which, in select embodiments, may be comprised of a pad or a sponge affixed to container 10, and, at least, partially covering seal 15. Applicator surface 30 is capable of absorbing and distributing flowable contents to facilitate application to a surface of interest.

Figure 2:
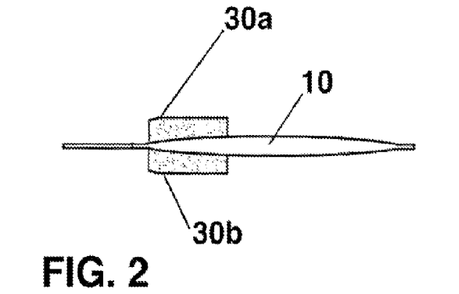
FIG. 2 is a side elevation of one dual absorptive surface embodiment of the present invention.
Figure 9:
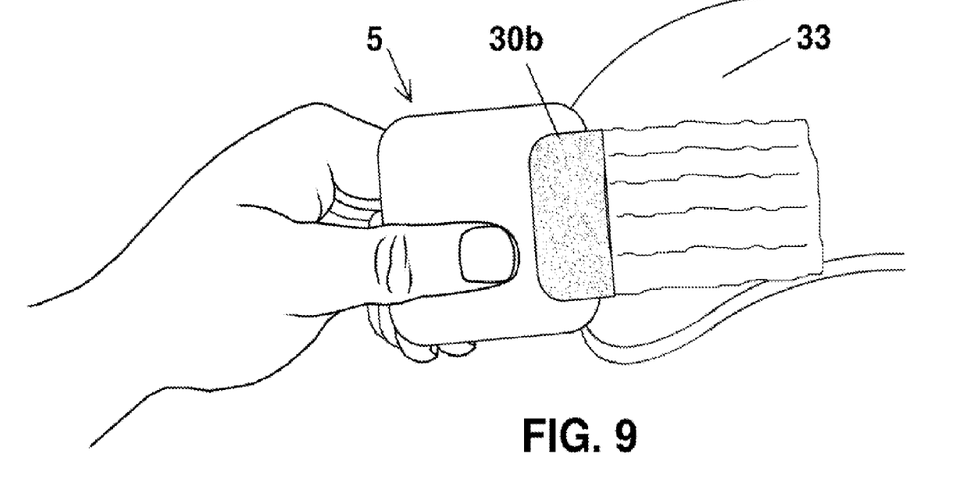
FIG. 9 is a perspective view illustrating an embodiment of the present invention, with the actuator tab removed, applying material to a surface of interest.

In one embodiment, illustrated by FIG. 2, two applicator surfaces 30a and 30b are affixed to the outer top and bottom surfaces of container pod 10, and in one embodiment surfaces 30 are sponges substantially rectangularly shaped and are oriented substantially parallel to container pod 10. Upon actuation of tab 20, material flowing from opening 25 is taken up by and distributed on said applicator 30. The applicator apparatus 5 may be used to distribute product in a side-to-side fashion, as illustrated by FIG. 9, wherein a user may place first applicator surface 30a in contact with an intended deposition surface 33 by rotating applicator 5 180 degrees from the position where the applicator surface 30b had been previously contacting the same destination surface 33.

Figure 3:
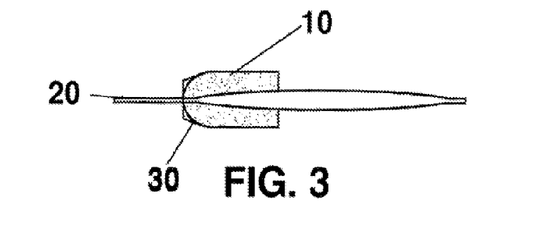
FIG. 3 is a side elevation view of one embodiment of the present invention illustrating absorptive surface around the front of the apparatus depicting the actuation tab passing through absorptive surface.
Figures 10, 11, 12:
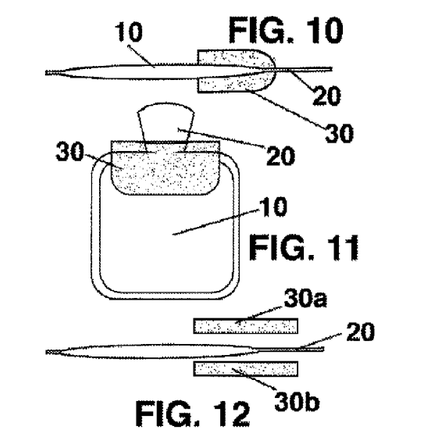
FIG. 10 is a side view of an embodiment of present invention illustrating absorptive surface affixed to the container pod and positioned around the front of the applicator apparatus with the actuation tab passing through a void in the absorptive surface.
FIG. 11 is a top view of an embodiment of present invention illustrating absorptive surface affixed to the container pod and positioned around the front of the applicator apparatus with the actuation tab passing through a void in the absorptive surface.
FIG. 12 is a partially exploded side view of an embodiment of present invention illustrating a dual absorptive surface.

In another embodiment, illustrated by FIG. 3, FIG. 10, and FIG. 11, applicator surface 30 is distributed around tab 20. One or more applicator surface 30 may be shaped to define a void 36 (fenestration) through which said actuating tab 20 passes; in certain embodiments, applicator surface 30 may be round. In one specific embodiment, applicator surface 30 is comprised of a substantially round sponge, wherein said void 36 is substantially centrally located, whereby two relatively semicircularly shaped portions of said sponge are affixed to said container pod 10. Applicator surface may be advantageously folded onto container pod 10 and adherently affixed thereto, preferably adhesively, such as by heat seal or glue-on-foil. When tab 20 is actuated and removed, material may flow from container pod 10 through opening 25 to become at least partially distributed on applicator surface 30. In this embodiment, applicator surface 30 may be used as a side-to-side applicator and front applicator, wherein the front aspect of applicator surface 30, illustrated by FIG. 4, may permit frontal application of material to an intended deposition surface, such as when a user dabs product forwardly on a specific location on the face.

Figures 23, 24, 25, 26, 27, 28:
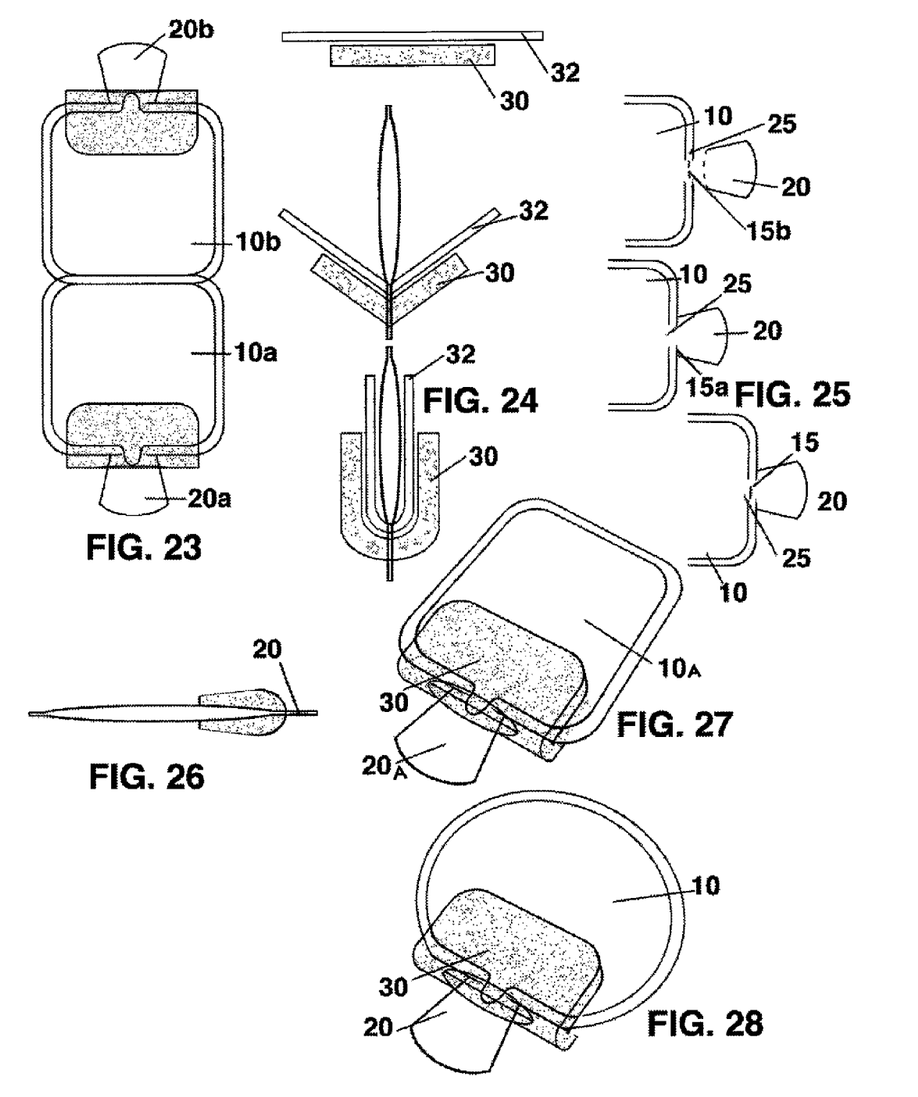
FIG. 23 is a top view of an embodiment of the applicator illustrating two joined container pods.
FIG. 24 is a side view of an embodiment of the present invention illustrating an example attachment between a stabilizer, container pod, and applicator surface.
FIG. 25 is a top view of embodiments of the present invention illustrating example openable seams.
FIG. 26 is a side view of an embodiment of the present invention illustrating a relatively large, full applicator surface.
FIG. 27 is a perspective view of an embodiment of the present invention.
FIG. 28 is a perspective view of an embodiment of the present invention illustrating rounded edges.

In another embodiment that may be adapted for application of material onto a relatively delicate surface tissue, such as the eye. A suitable applicator surface 30, such as a relatively soft, large, or smooth surface, exemplified by FIG. 26 is utilized. Further, tear strip 25 may be concavely shaped relative to the applicator surface to aid in avoiding seam contact with the delicate tissue surface—irrespective of the thickness of applicator surface 30 of the amount axial pressure exerted by the user. In use, actuation of tab 20 opens pod container 10 and material is distributed to applicator surface 30. This surface may be placed in contact with the surface of the eye to permit, for example, the delivery of substances believed to have therapeutic benefits thereon—such as Amino-Plex® as a method for reducing ocular irritation following exposure to irritative agents.

In other embodiments, the present invention may utilized in a therapeutic setting. For example, pharmaceuticals, nutraceuticals, and medicinal agents such as, for example Amino-Plex®, may be placed by applicator 5 on skin or tissue surfaces (including surgical or non-surgical wound sites) to promote healing following, for example, common recreational tattooing, or therapeutic treatment of diabetic dermatological sores. As additionally demonstrative, the present inventive applicator 5 may be used to package and apply a therapeutic petroleum balm, with precision, to a specific tissue or skin. For example, the inventive applicator may be used with topical wound care products, for example, such as Tattoo Genie® containing Amino-Plex® which is designed to provide improved healing and retained coloration in newly placed tattoos. Embodiments of the present invention provide a consecutive methodology for applying substances to a desired surface, wherein container 10 has more than one compartment, and the contents of each compartment may be expelled to a destination surface serially. An example of consecutive application methodology may be illustrated by a tattoo aftercare protocol calling for the utilization of petroleum balm and Amino-Plex®. Turning now to FIG. 1, in this example, petroleum balm, may be placed in compartment 40a and Amino-Plex® placed in compartment 45a. The user first actuates tab 20 and compresses container 10 over compartment 40a. When the material has been substantially deposited on the skin's surface, the user places compressible pressure over compartment 45a sufficient to rupture seal 50, permitting Amino-Plex® to flow from compartment 45b onto the skin's surface. This method may be reversed, with Amino-Plex® being placed in compartment 40a and first deposited onto skin followed by petroleum balm in compartment 45a. Of course, it will be noted that the preceding example is not limiting, but rather illustrative of a consecutive application method using a dual compartment embodiment inventive applicator 5 applying materials to a designated surface which may be used for any substances to be applied sequentially. Further, it should be noted that various embodiments of applicator 5 may be contained within secondary packaging to maintain product sterility and cleanliness.

Figure 14:
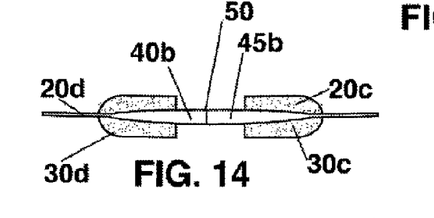
FIG. 14 is a side view of an embodiment dual chamber apparatus illustrating an optional dividing seam.
Figure 15:
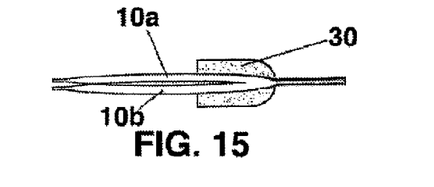
FIG. 15 is a side view of a dual container pod embodiment utilizing a single applicator surface.

In one embodiment, container pod 10 is comprised of a flexible foil packaging. In one embodiment, as illustrated by FIG. 1, container pod 10 may be divided into one or more sealed compartments, such as example compartments 40 and 45 by rupturable seal 50, sealing at least two compartments of said container from each other. FIG. 14 illustrates an embodiment having a rupturable seal 50 in the center between two opposing ends having individual actuator tabs 20c and 20d, and individual application surfaces 30c and 30d. Upon application of a sufficient compressible force on one or both compartments, seal 50 is ruptured and contents of compartment 40 and 45 are mixed. It follows that the force sufficient to disrupt seal 50 is less than the force required to rupture container pod 10 itself or perimetrical seal 12. The divided container embodiment has particular application in circumstances, for example, where it is desirable to mix two substances shortly before intended use. The number of compartments, as well as size and shape of each compartment is variable. Further, one or more compartments may be filled with a solid or semisolid material that mixes with or becomes flowable upon contact with material from one or more other chambers after seal 50 is broken.

In one embodiment, partially illustrated by FIG. 23, two individual container pods 10a and 10b may be joiningly affixed end to end, wherein a second sealed flexible container having a top surface, bottom surface, front surface, and end surface. The second container has a its own openable seal (second openable seal); its own actuating tab operatively connected to said openable seal (second actuating tab); wherein when said tab is pulled with sufficient force, said second openable seal is broken sufficiently to permit contents within said container to flow out therefrom and material contained in container and second container respectively may be distributed to an embodiment round sponge. Actuating tab 20a and second actuating tab 20b pass through the centrally located void of said sponge. The container 10 and second container are affixed in a substantially overlapping position, wherein said actuating tab and said second actuating tab pass through the void of said sponge. This embodiment permits identical, similar, or entirely different products to be packaged together, yet contained separately. In a specific embodiment, illustrated by FIG. 27, container pods 10a and 10b may be opposed and affixed together in a substantially overlapping position and share applicator surface 30. In an alternative embodiment, the second container has its own applicator surface. Container 10a and 10b may have individual tabs 20a and 20b as illustrated by FIG. 23, or in an alternative embodiment may share the same tab 20. It should be noted, however, that FIG. 23 illustrates an embodiment bearing two applicator surfaces. In a preferred embodiment, illustrated by FIG. 27, both actuation tabs 20a/20b pass through a void located in a single applicator surface 30. When tab 20a or 20b is actuated, material from the corresponding container may be distributed on applicator surface 30; where both are actuated simultaneously, material from each is distributed on applicator surface 30. Alternatively, when tab 20 (of the single tab alternative embodiment) is actuated, such action opens container pods 10a and 10b which permit material to flow from both container pods and become mixed and distributed on application surface 30. These embodiments, therefore, permit efficient manufacture and packaging of either single or multiple container pods 10, and provides convenient point-of-use mixing and application of material.

Figure 16:
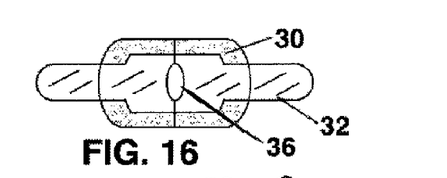
FIG. 16 is top view of an embodiment unfolded stabilizer affixed to an unfolded applicator surface illustrating the void in both.
Figures 17, 18:
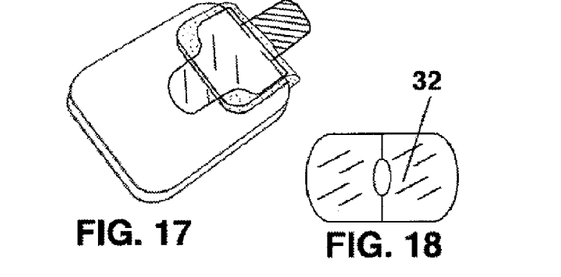
FIG. 17 is a perspective view of an embodiment of the present invention.
FIG. 18 is a top view of an optional embodiment stabilizer.

Turning now to FIGS. 16, 17, 18, and 24, in specific embodiments, one or more applicator surface 30 may be mounted on a rigid or semi-rigid stabilizer 32, and stabilizer 32 is affixed to container pod 10, as illustrated by FIG. 24. Stabilizer 32 is indirectly affixed to container 10, to provide a relatively rigid plastic stabilizer 32 having a first surface and second surface, the first surface of which affixed to container 10, the second surface of which affixed to said applicator surface 30. Stabilizer 32 decreases container 10 and applicator surface 30 bending, provides a degree of firmness to applicator surface 30 during application of material to a suitable deposition surface, and is particularly helpful in circumstances where applicator surface 30 is relatively heavy and tends to cause kinking or bending of container 10 which may obstruct flow from contents within. Further, stabilizer 32 may have the effect of stabilizing openable seal 15 prevent container pod 10 from tearing in a location other than the intended seal; this is particularly true where container pod 10 is comprised of a relatively thin or flexible material. A variety of stabilizer 32 shapes and sizes may be advantageously used as illustrated by FIGS. 16-18.

It should be noted that in most embodiments openable seal 15 is proximal to the most distal edge of applicator surface 30, such that when container 10 is opened and actuating tab 20 removed, the open portion of container 10 is relatively deep within applicator surface 30, such that the most distal portion of container pod 10 or seal 15 is not readily exposed to the user (See, e.g. FIG. 9), even where user applies a modest degree of pressure to the frontalmost aspect of the applicator surface. In an alternative embodiment, openable seal 15 may be aligned with, or permitted to protrude beyond applicator surface 30 such that it comprises the distal edge of apparatus 5; this embodiment is particularly useful in cases where it is desirable to have a small amount of product directly accessible to the user.

Figure 29:
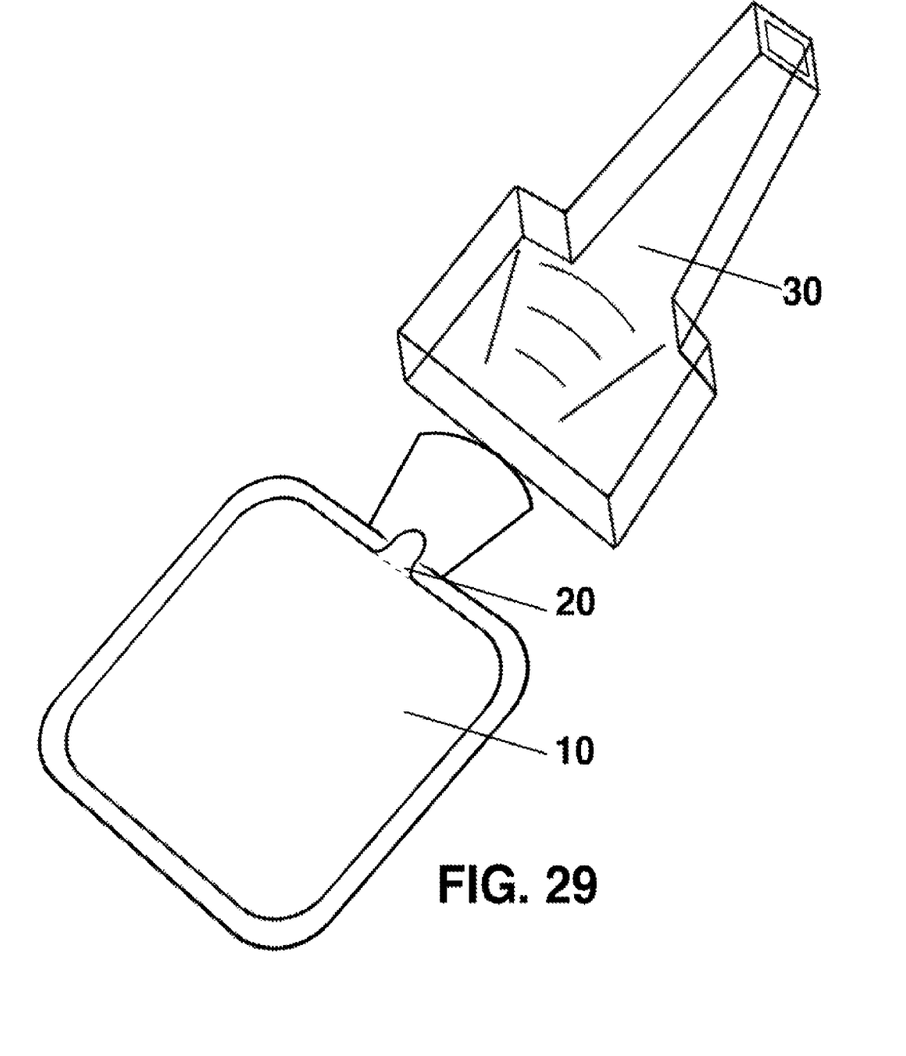
FIG. 29 is an exploded perspective view of an alternative embodiment applicator surface.

With reference to FIG. 29, in another embodiment, applicator surface 30 is comprised of rigid, tapering hollow plastic jacket 30j which is placed over container pod 10 having openable seal 15 located within. Actuator tab 20 is elongated, the terminal aspect of which projects through the distal end of surface 30j. When tab 20 is actuated, product is released into and collected within a portion of jacket 30j and dispensed through the terminal end of the same. In this way, jacket 30j serves as a pinpoint applicator and will stabilize attached packaging. Further, in an embodiment where container pod 10 is divided by a rupturable seam, as illustrated by FIG. 1, jacket 30j will additionally function as a mixing chamber.

The present invention further discloses a method for applying a substance to an intended surface. The inventive method involves: selecting the appropriate surface, selecting an appropriate material to apply to said surface; providing a container and applicator having: a container 10, an openable seal 15, an actuating tear tab 20, and an applicator surface 30, wherein when said tab is pulled with sufficient force, said seal is ruptured and creates an opening in container pod, wherein said container may hold material which may be naturally flow from, be expressed from, or extruded through the opening, wherein said applicator surface absorbs and distributes said material throughout said applicator surface facilitating application to a surface of interest; actuating said tear tab, placing applicator surface in contact with intended deposition surface, whereby material will be transferred from said applicator surface to said deposition surface. In some cases, the material will readily pass through opening 25 and be adequately distributed on applicator surface.

In other cases, the user may assist distribution on said applicator surface through the additional step of inverting said container after said tear tab has been actuated, wherein said opening substantially faces the ground, whereby gravity will facilitate flowable material passing from within said container to said applicator surface. The method may include the additional step of manually compressing the container pod to increase inter-container pressure, whereby material more readily flows from, is expressed or extruded from said container pod and distributed on said applicator surface.

Tab 20 may be comprised of a single layer of material or may be comprised of two layers of material in opposition but perimetrically sealed. Alternatively, tab 20 may form part of the functional container when sealed.

Openable seal, 15, in one preferred embodiment, in part illustrated by FIG. 25, a notch cut 15a on either side of container pod 10 underneath applicator surface 30. In another embodiment, seal 15 may be comprised of a tear strip formed by microperforations 15b (FIG. 25) along the container corresponding to the desired size of the opening 25 after tab 20 has been actuated. Other examples of suitable tear strips include, but are not limited to, notching closely formed and preferentially directed in a tearing direction parallel with the direction of the molecular orientation of the container material, heat welding a strip to the outer surface of a container wall, the use of a weakened material to substantially delineate the tearing path. The extent of desired package opening is variable, and may depend on the nature and absorptive and distributive characteristics of the applicator itself. The size and nature of opening 25 may also depend on physical properties of the contained material (such as viscosity, cohesive and adhesive forces), as well as expected volume of demand, anticipated use of the material, and the varied anticipated individual needs of the target user base. Openable seal 15 may be straight relative to the frontmost surface of the applicator surface, or in various embodiments may be convex, concave, or irregular.

Figures 4, 5, 6, 7, 8:
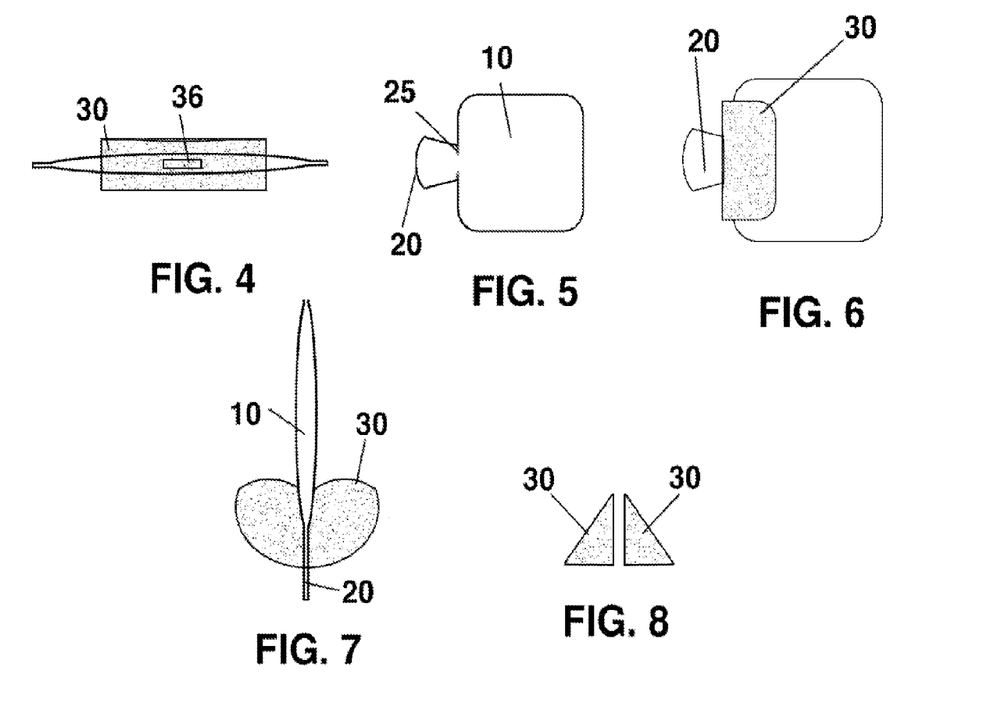
FIG. 4 is a front view of one embodiment of the present invention illustrating actuation tab passing through the absorptive surface.
FIG. 5 us a top view of one embodiment of the present invention illustrating the location of the opening and actuation tab.
FIG. 6 is a top view of an embodiment illustrating a rectangular absorptive surface and wide actuating tab.
FIG. 7 is a perspective view illustrating an optional embodiment where the applicator surface is peeled away from the container pod.
FIG. 8 is a side view illustrating embodiment wedge-shaped applicator surfaces.
Figure 13:
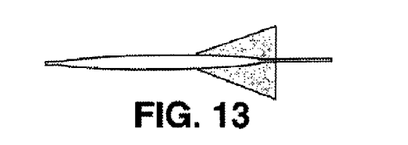
FIG. 13 is a side view of an embodiment of the present invention illustrating a relatively wide applicator surface.
Figures 19, 20, 21:
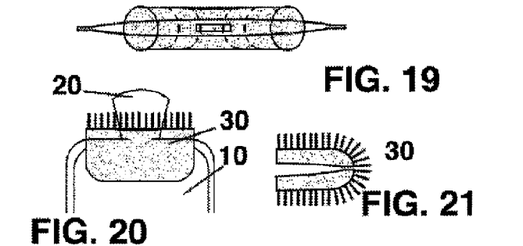
FIG. 19 is a front view of an embodiment of the present invention.
FIG. 20 is a top view of an embodiment of the present invention illustrating an optional brush-like applicator surface.
FIG. 21 is a side view of an embodiment applicator surface illustrating flocking material.
Figure 22:
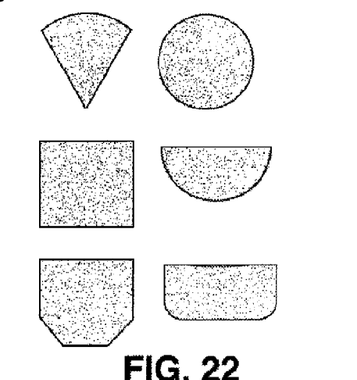
FIG. 22 is a top view illustrating example alternative embodiment applicator surface shapes.

Regarding applicator surface 30, said surface may be comprised of any substance that permits at least some distribution of material on a an ideal deposition surface, and will depend on the material being applied to that surface. For example, open-cell sponges will readily absorb fluid material and may be well suited where it is intended that applicator surface 30 itself absorb fluid material. In contrast, closed-cell sponges will be relatively non-absorbent; this may advantageously reduce bacterial colonization where an applicator is used over a relatively extended period of time. In other instances, it may be advantageous that applicator surface 30 be impermeable. The desirable degree of applicator surface 30 wetting, in fact, will be dependent upon the type and physical characteristics of fluid utilized, the anticipated use of the fluid, and an array of other factors, including specific consumer use characteristics. Thusly, a variety of applicator surface sizes and shapes may be utilized, including, as an example, a taper-cut sponge which tapers from wide to narrow to facilitate relatively pinpoint application of material. FIGS. 13 and 19 illustrate a side view and front view of a relatively wide applicator surface embodiment. FIG. 22 illustrates a non-limiting example of applicator surface shapes, including but not limited to wedge, round, square, semicircular, polygonal, triangular, conical, and irregular. FIG. 8 illustrates a wedge shaped tapering applicator surface embodiment, wherein sponges taper from wide to narrow, the narrowest portion being furthest from container 10. Further, a variety of applicator surface characteristics, including but not limited to permeability, absorption, degree of hydrophilia/hydrophobia, softness, resiliency, resistance to tearing, and bacterial colonization may be taken into consideration when selecting an appropriate applicator surface for a particular fluid and use.

Now, referring to FIG. 20, in one embodiment, an applicator surface 30 may be brush-like and permit filamentous distribution of material. FIG. 21 illustrates an embodiment applicator surface 30 that may be comprised of a sewn in soft-flock material.

Container pod 10 may be comprised of any material that is capable of holding flowable materials such as, for example, plastic. The present invention permits container pod 10 to be customizable with regard to container pod physical characteristics such as, for example, size, shape, volume, coloration, transparency, and resiliency. Container pod 10 may be of any shape, including, specifically cylindrical; and in one specific embodiment a cylindrical container pod 10 having a conical absorption surface 30. Further, FIG. 28 illustrates an embodiment container pod 10 having rounded edges.

Regarding the method of affixation of applicator surface 30 to container pod 10, example methods include, but are not limited to heat sealing or glue on foil. The present invention may be practiced with any method permitting surface 30 to be affixed to container pod 10. In some embodiments, it may be intended that the affixation is releasable and reversible and the user can selectively peel away (and optionally reaffix) applicator surface 30, as partially illustrated by FIG. 7, without compromising pod 10 or surface 30; in other embodiments affixation may be permanent.

Although the present invention has been described with reference to the preferred embodiments, it should be understood that various modifications and variations can be easily made by those skilled in the art without departing from the scope and spirit of the invention. Accordingly, the foregoing disclosure should be interpreted as illustrative only and is not to be interpreted in a limiting sense. It is further intended that any other embodiments of the present invention that result from any changes in application or method of use or operation, method of manufacture, shape, size, or material which are not specified within the detailed written description or illustrations contained herein yet are considered apparent or obvious to one skilled in the art are within the scope of the present invention.

What is claimed is:

1. An applicator comprising:
   a sealed container, said container having a top surface, bottom surface, front surface, and end surface, said container having an openable seal;
   an actuating tab operatively connected to said openable seal;
   at least one applicator surface affixed to said container and at least partially covering openable seal;
   wherein when said tab is pulled with sufficient force, said openable seal is broken sufficiently to permit contents within said container to flow out and be distributed onto said applicator surface a second sealed flexible container, said container having a top surface, bottom surface, front surface, and end surface, said second container having a second openable seal; a second actuating tab operatively connected to said second openable seal; wherein when said second tab is pulled with sufficient force, said second openable seal is broken sufficiently to permit contents within said second container to flow out and be distributed onto said applicator surface, wherein said applicator surface is shaped to define a centrally located void, wherein the actuating tab and second actuating tab pass through the centrally located void of said applicator surface.

2. An applicator comprising:
   a sealed flexible first container, said container having a top surface, bottom surface, front surface, and end surface;
   a sealed flexible second container said second container having a top surface, bottom surface, front surface, and end surface;
   said first container and second container sharing an openable seal;
   an actuating tab operatively connected to said openable seal;
   at least one applicator surface at least a portion of which affixed to said first container and at least a portion of which affixed to said second container, said applicator surface at least partially covering said openable seal;

wherein when said tab is pulled with sufficient force, said openable seal is broken sufficiently to permit contents within said first container and second container to flow therefrom and be distributed onto said applicator surface.

3. An applicator comprising:
a first sealed container, said first container having a first container top surface, a first container bottom surface, a first container front surface, and a first container end surface, said first container having a first container openable seal;
a first container actuating tab operatively connected to said first container openable seal;
a first applicator surface affixed to said first container, wherein the first applicator surface is shaped to define a first centrally located void, wherein the first actuating tab passes through the first centrally located void of the first applicator surface;
a second sealed container, said second container having a second container top surface, a second container bottom surface, a second container front surface, and a second container end surface, said second container having a second openable seal;
a second actuating tab operatively connected to said second container;
a second applicator surface affixed to said second container, wherein the second applicator surface is shaped to define a second centrally located void, wherein the second actuating tab passes through the second centrally located void of the second applicator surface;
wherein said second container is affixed to said first container;
wherein when said first tab is pulled with sufficient force, said first openable seal is broken sufficiently to permit contents within said first container to flow out and be distributed onto said first applicator surface, wherein when said second tab is pulled with sufficient force, said second openable seal is broken sufficiently to permit contents within said container to flow out and be distributed onto said second applicator surface.

\* \* \* \* \*